United States Patent

Liaw et al.

[11] Patent Number: 6,137,008
[45] Date of Patent: Oct. 24, 2000

[54] FLEXIBLE DIAMINE COMPOUND FOR PREPARATION OF POLYAMIDE AND POLYIMIDE

[75] Inventors: Der-Jang Liaw; Been-Yang Liaw, both of Taipei, Taiwan

[73] Assignee: National Science Council, Taiwan

[21] Appl. No.: 09/324,295

[22] Filed: Jun. 2, 1999

Related U.S. Application Data

[60] Continuation-in-part of application No. 09/082,974, May 21, 1998, abandoned, which is a division of application No. 08/855,963, May 14, 1997, Pat. No. 5,817,741.

[51] Int. Cl.[7] .................................................. C07C 217/86
[52] U.S. Cl. ..................... 564/315; 528/170; 528/172; 528/173; 528/174; 528/176; 528/183; 528/185; 528/188; 528/220; 528/229; 528/310; 528/332; 528/335; 528/350; 528/353
[58] Field of Search ............................ 564/315; 528/170, 528/172, 173, 174, 176, 183, 185, 188, 220, 229, 310, 332, 335, 350, 353

[56] References Cited

U.S. PATENT DOCUMENTS

| | | | |
|---|---|---|---|
| 4,410,684 | 10/1983 | Nelb et al. | 528/310 |
| 5,032,667 | 7/1991 | Harris et al. | 528/353 |
| 5,037,949 | 8/1991 | Mueller et al. | 528/353 |
| 5,069,556 | 12/1991 | Sasaki et al. | 347/19 |
| 5,132,711 | 7/1992 | Shinda et al. | 347/6 |
| 5,363,134 | 11/1994 | Barbehenn | 347/49 |

OTHER PUBLICATIONS

Sase et al. Chem. Abst. 117:251967, 1992.

*Primary Examiner*—Peter O'Sullivan
*Attorney, Agent, or Firm*—Fish & Richardson P.C.

[57] ABSTRACT

A diamine which is useful in preparing a new flexible polyamide and polyimide with an aromatic dicarboxylic acid and a tetracarboxylic dianhydrides, respectively, has a general formula as follows:

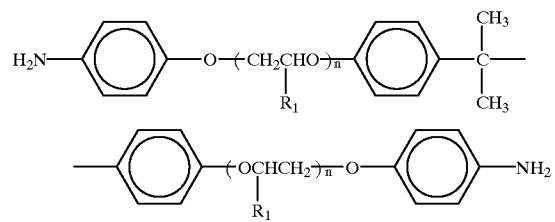

wherein $R_1$ is methyl ($-CH_3$) and n is an integer ranging from 1 to 4. These polyamide and polyimide exhibit good mechanical performance and processability

2 Claims, No Drawings

FLEXIBLE DIAMINE COMPOUND FOR PREPARATION OF POLYAMIDE AND POLYIMIDE

CROSS REFERENCE TO THE RELATED APPLICATIONS

This is a continuation-in-part application of an application Ser. No. 09/082,974, filed May 21, 1998, now abandoned, which is a divisional application of an application Ser. No. 08/855,963, filed May 14, 1997, now U.S. Pat. No. 5,817,741.

BACKGROUND

The present invention relates to a diamine compound, and in particular to a diamine compound having two terminated amino groups and flexible oxypropylene linkage.

Wholly aromatic polyamides and polyimides are well established as high-performance materials with excellent thermal stability and mechanical properties. However, these polymers have a demerit of fabrication problem due to their limited solubility and their high melt or softening temperatures. For example, poly(p-phenyleneterephthalamide) (Kevlar), a well known commercial product and used as a high modulus fiber for a variety of applications, is infusible and only soluble in concentrated sulfuric acid. The infusibility and limited solubility of these aromatic polymers are characteristic properties which restrict synthesis, characterization, processing, and applications thereof, especially to those of high molecular weight. Therefore, a great deal of effort has made for improving their processability.

For instance, the incorporation of flexible linkages, such as arylene ether (—O—) [EP 0565352 A2, JP 05262705], methylene (—CH$_2$—) [EP 0483954 A1], sulfone (—SO$_2$—) [JP 05295262], isopropylidene [—C(CH$_3$)$_2$—)] [U.S. Pat. No. 4,410,684, JP 04183721], and siloxane (—Si—O—) [JP 05214100, JP 04189867] into the polymer backbone to increase the overall chain flexibility are disclosed. The presence of flexible segments can decrease the glass transition temperature and/or the melting temperature and in some cases can even improve the solubility of polyamides and polyimides; thus, processable polymers can be obtained. The polymer structural modifications adopted in the prior art were usually employed by the insertion of flexible segments to the diamine monomer which is to be polycondensated with an aromatic dicarboxylic acid or a tetracarboxylic dianhydride to form the polyamide and polyimide, respectively.

SUMMARY

The present inventors synthesize a diamine compound containing both flexible isopropylidene and oxypropylene linkages in this invention, which can be used to prepare polyamides and polyimides having a higher Tg and a lower degree of crystallinity compared to those prepared with a diamine compound containing an oxyethylene linkage. Surprisingly, the polyimides prepared with the diamine of the present invention is soluble in most of the organic solvents in contrast with insolubility shown by the polyimides prepared with the diamine compound containing an oxyethylene linkage.

Said flexible diamine compound synthesized in accordance with the present invention has the following structure:

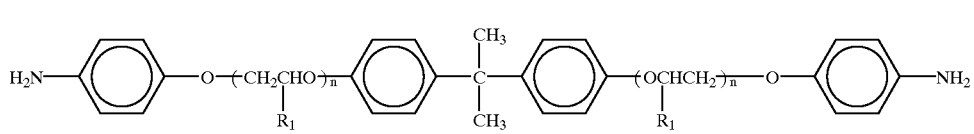

(I)

wherein R$_1$ is a methyl (—CH$_3$); and n is an integer of 1–4, preferably n is 1.

The present invention also discloses a series of polyamides and polyimides having good mechanical strength and/or soluble or melting processability, which are prepared by conducting polycondensation reactions of said flexible diamine and various dicarboxylic acids and various aromatic dianhydrides.

Said polyamides and polyimides can be represented by a general formula as follows:

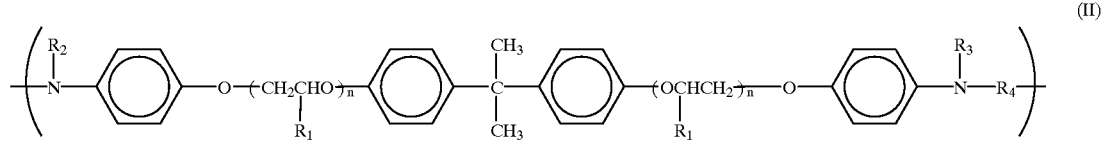

(II)

wherein R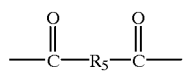 and n are the same as above; and (i) R$_2$ and R$_3$ both are protons (—H), and R$_4$ is:

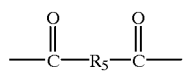

wherein R$_5$ is

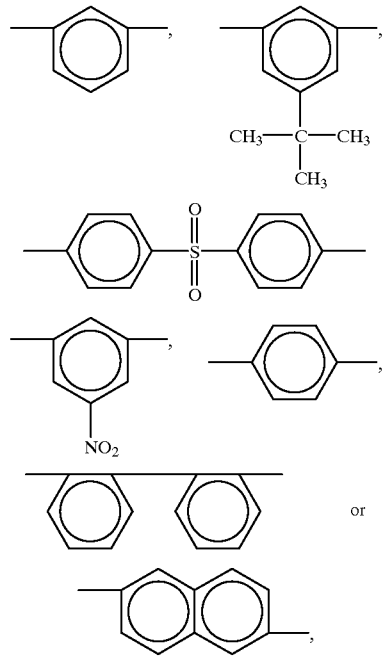

or (ii) R$_2$ represents a single bond, and R$_3$ and R$_4$ cooperatively have the following structure:

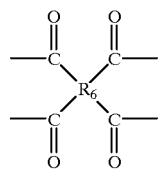

wherein R$_6$ is:

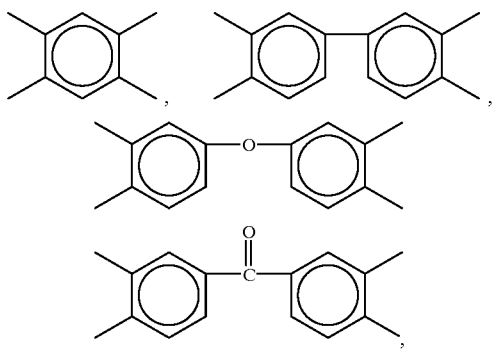

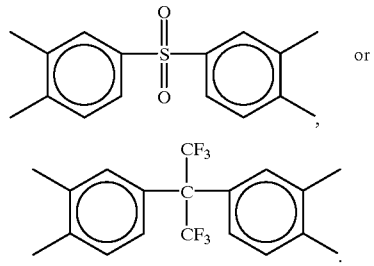

The polyimide synthesized according to the present invention preferably have an inherent viscosity of 0.65–0.89 dL g$^{-1}$, measured in concentrated H$_2$SO$_4$ (98%) at a concentration 0.5 g dL$^{-1}$ at 30° C.

DETAILED DESCRIPTION OF THE PREFERRED EMBODIMENTS

The starting flexible diols can be condensated from ethylene carbonate or propylene carbonate with bisphenol-A in the presence of sodium carbonate at 180–220° C. The chemical reaction can be shown as follows:

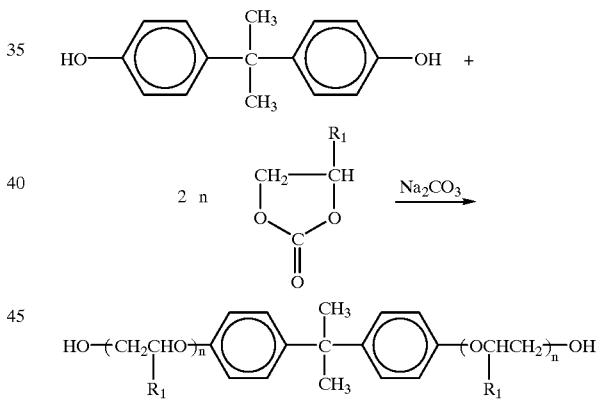

wherein R$_1$ is methyl (—CH$_3$); and n is an integer ranging from 1 to 4. In other words, the flexible diols include the following: bis(4-(2-hydroxypropoxy)phenyl)propane, bis(4-(2-(2-hydroxypropoxy)-propoxy)phenyl)propane, bis(4-(2-(2-(2-hydroxypropoxy)-propoxy)propoxy)phenyl)propane, and bis(4-(2-(2-(2-(2-hydroxypropoxy)-propoxy)propoxy)propoxy)phenyl)propane.

The flexible chain-containing diamines of the present invention can be prepared by thermocondensing various flexible diols with p-chloronitrobenzenes in a polar solvent of inorganic base, followed by a hydrogenated reduction. The chemical reactions can be shown as follow:

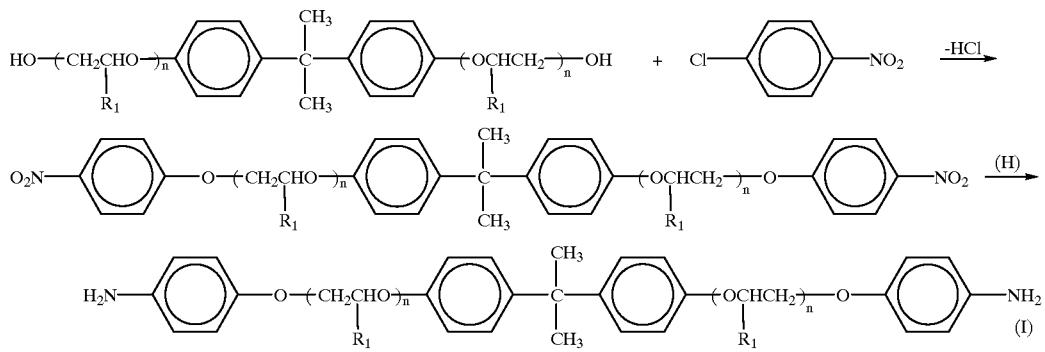

In other words, the diamines include the following: 2,2-bis [4-[2-(4-aminophenoxy)propoxy]phenyl]-propane, 2,2-bis [4-[2-(2-(4-aminophenoxy)propoxy)propoxy]-phenyl] propane, 2,2-bis[4-[2-(2-(2-(4-aminophenoxy)propoxy)-propoxy)-propoxy]phenyl]-propane, and 2,2-bis[4-[2-(2-(2-(2-(4-aminophenoxy)propoxy)propoxy)propoxy)propoxy] phenyl]propane.

The condensation reaction for removing HCl can be completed by a heating reaction in the aprotic solvent (DMF (dimethylformamide) or NMP (N-methyl-2-pyrrolidone)) to which potassium carbonate is added. The hydrogenated reduction is able to be readily carried out in a hydrazine/Pd—C system.

The flexible diamine (I) of the present invention is useful for preparing polymers such as polyamides and polyimides, and the preparing methods thereof are described in the following.

The polyamide can be synthesized by polycondensating the flexible diamine (I) with a dicarboxylic acid in aprotic solvent such as NMP. When the flexible diamine (I) directly reacts with the dicarboxylic acid, we may use a condensing agent to carry out the polycondensation. One of the most suitable condensing agents is a triphenyl phosphite-pyridine system. The polycondensation reaction is shown as follows:

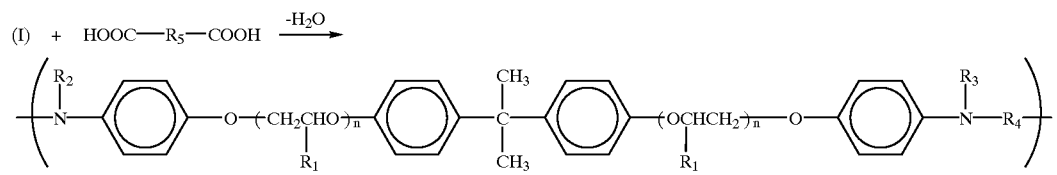

wherein $R_1$, $R_2$, $R_3$, $R_4$, $R_5$ and n are as described in the Summary. The dicarboxylic acid used, for example, can be any one of the following: isophthalic acid, 5-t-butylisophthalic acid, 4,4'-sulfonyldibenzoic acid, 5-nitroisophthalic acid, terephthalic acid, diphenic acid, and 2,6-naphthalic acid.

The polyimide can be prepared by the polyaddition of the diamine (I) and an dianhydride in a proper organic solvent to form a poly(amic acid). Then the poly(amic acid) is heated or is mixed with a dehydrating agent to form the polyimide. The chemical reaction equation is as follows:

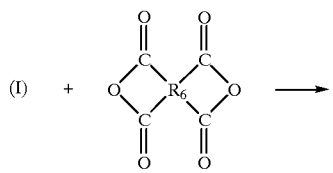

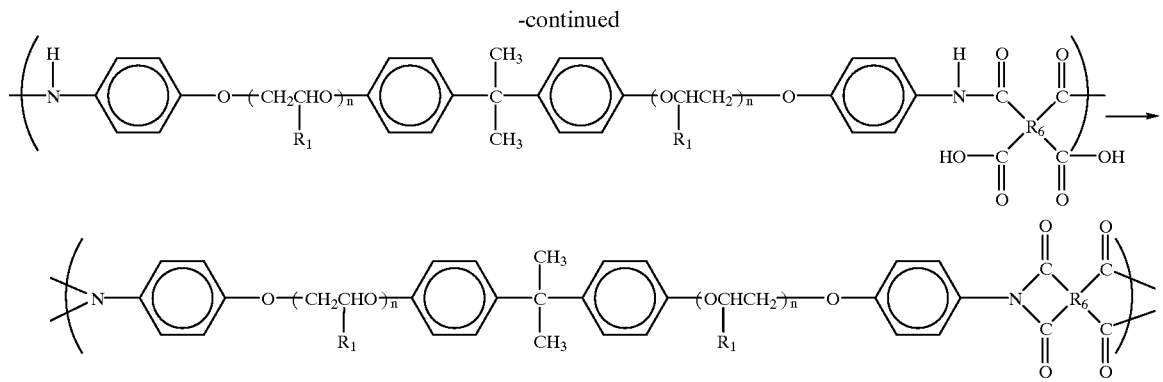

wherein $R_1$, $R_6$ and n are as described in the Summary. The dianhydride used, for example, can be one of the following: pyromellitic dianhydride (PMDA), 3,3',4,4'-biphenyltetracarboxylic dianhydride (BPDA), 4,4'-oxydiphthalic anhydride (OPDA), 3,3',4,4'-benzophenonetetracarboxylic dianhydride (BTDA), 4,4'-sulfonyldiphthalic anhydride (DSDA), and 4,4'-hexafluoro-isopropylidenebisphathalic anhydride (6FDA).

This invention is more specifically described by the following illustrative examples.

PREPARATIVE EXAMPLE 1

A spherical flask (500 mL), equipped with a reflux condenser, stirrer, thermometer, and nitrogen inlet, was charged with bisphenol A (45.6 g, 0.2 mol), ethylene carbonate (35.2 g, 0.4 mol), and sodium carbonate (0.2 g) as catalyst. The mixture was heated to 165–170° C. under nitrogen for 2 hours. The crude product was washed with water several times to remove unreacted ethylene carbonate and recrystallized from methanol. A white crystalline product, m.p. 105° C., was obtained in a yield about 86%. The IR spectrum (KBr) exhibited absorption at 3400 cm$^{-1}$ (—OH), 2800–2950 cm$^{-1}$ (CH$_2$). $^{13}$C-NMR (CDCl$_3$): δ (ppm)=31.36, 42.15, 61.36, 70.37, 114.68, 128.40, 143.82, 157.83.

The product, bis(4-(2-hydroxyethoxy)phenyl)propane, has the following molecular structure:

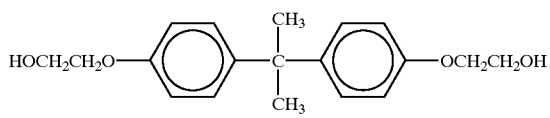

PREPARATIVE EXAMPLE 2

A spherical flask (500 mL), equipped with a reflux condenser, stirrer, thermometer, and nitrogen inlet, was charged with bisphenol A (45.6 g, 0.2 mol), propylene carbonate (42 g, 0.4 mol), and sodium carbonate (0.2 g) as catalyst. The mixture was heated to 200–210° C. under nitrogen for 4 hours. the crude product was washed with water several times. A yellow viscous product was obtained in a yield about 90%. The IR spectrum (KBr) exhibited absorption at 3400 cm$^{-1}$ (—OH), 2800–2950 cm$^{-1}$ (CH$_2$). $^{13}$C-NMR (CDCl$_3$): δ (ppm)=15.63, 30.68, 41.32, 65.57, 74.35, 115.08, 127.39, 141.20, 155.60.

The product, bis(4-(2-hydroxypropoxy)phenyl)propane, has the following molecular structure:

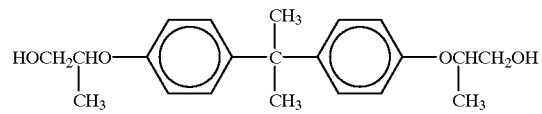

PREPARATIVE EXAMPLE 3

A spherical flask (500 mL), equipped with a reflux condenser, stirrer, and thermometer, was charged with [2,2-bis(4-β-hydroxyethoxy)phenyl]propane 79.0 g (0.25 mol), p-chloronitrobenzene 81.9 g (0.52 mol), potassium carbonate 79.4 g (0.57 mol) and DMF 300 mL. The mixture was heated at 160° C. for 8 hours. The mixture was then cooled and poured into a mixture of methanol/water (1:1 by volume). The crude product was recrystallized from glacial acetic acid to provide yellow needle (m.p. 126–127° C.) in 83% yield. The IR spectrum (KBr) exhibited absorption at 1587 and 1331 cm$^{-1}$ (NO$_2$), 1241 cm$^{-1}$ (C—O—C).

Elemental analysis data: calc. C, 66.67%; H, 5.38%; N, 5.02%; found: C, 65.88%; H, 5.54%; N, 4.78%.

The product, 2,2-bis[4-[2-(4-nitrophenoxy)ethoxy]phenyl]-propane, has the following molecular structure:

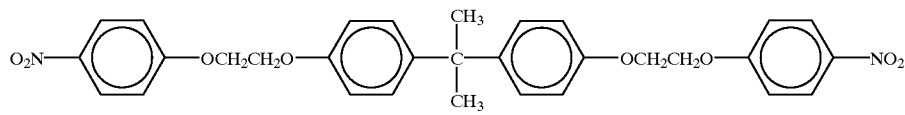

PREPARATIVE EXAMPLE 4

A spherical flask (500 mL), equipped with a reflux condenser, stirrer, and thermometer, was charged with [2,2-bis(4-β-hydroxypropoxy)phenyl]propane 86 g (0.52 mol), p-chloronitrobenzene 81.9 g (0.52 mol), potassium carbonate 79.4 g (0.57 mol) and DMF 300 mL. The mixture was heated at 160° C. for 8 hours. The mixture was then cooled and poured into a mixture of methanol/water (1:1 by volume). The crude product was recrystallized from glacial acetic acid to provide yellow needle (m.p. 102° C.) in 78% yield. The IR spectrum (KBr) exhibited absorption at 1582 and 1330 cm$^{-1}$ (NO$_2$), 1243 cm$^{-1}$ (C—O—C).

Elemental analysis data: calc.: C, 67.33%; H, 6.16%; N, 4.76%; found: C, 67.02%; H, 6.01%; N, 4.81%.

The product, 2,2-bis[4-[2-(4-nitrophenoxy)propoxy]phenyl]-propane, has the following molecular structure:

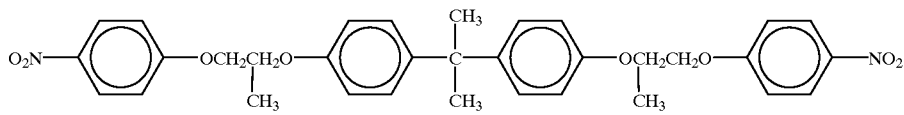

EXAMPLE 1

7.5 g (14.0 mmol) of the dinitro compound obtained from the preparative example 3, 0.04 g of 10% Pd—C, and 60 mL ethanol were introduced into a three-necked flask to which hydrazine monohydrate (20 mL) was added dropwisely over a period of 1 hour at 85° C. After the addition was complete,

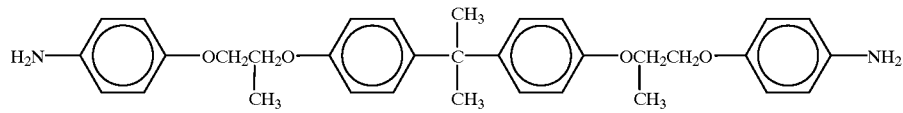

the reaction was continued under reflux for another 24 hours. The mixture was then filtered to remove Pd—C. After cooling, the precipitated crystals were isolated by filtration and recrystallized from ethanol in 86% yield (m.p. 117–118° C.). The IR spectrum (KBr) exhibited absorption at 3388 and 3310 cm$^{-1}$ (N—H), 1236 cm$^{-1}$ (C—O—C). $^1$H and $^1$C-NMR spectra of diamine in DMSO-d$_6$ appear in FIGS. 1 and 2, respectively.

Elemental analysis data: calc. C, 74.70%; H, 6.83%; N, 5.62%; found: C, 74.72%; H, 6.82%; N, 5.58%.

The product, 2,2-bis[4-[2-(4-aminophenoxy)ethoxy]phenyl] propane, has the following molecular structure:

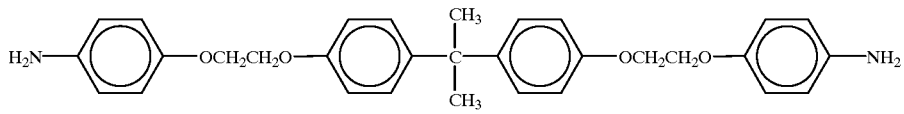

EXAMPLE 2

8.2 g (14 mmol) of the dinitro compound obtained from the preparative example 4, 0.04 g of 10% Pd—C, and 50 mL ethanol were introduced into a three-necked flask to which hydrazine monohydrate (20 mL) was added dropwisely over a period of 1 hour at 85° C. After the addition was complete, the reaction was continued under reflux for another 24 hours. The mixture was then filtered to remove Pd—C. After cooling, the precipitated crystals were isolated by filtration and recrystallized from ethanol in 79% yield (m.p. 97° C.). The IR spectrum (KBr) exhibited absorption at 3341 and 3321 cm$^{-1}$ (N—H), 1230 cm$^{-1}$ (C—O—C).

Elemental analysis data: calc.: C, 78.83%; H, 8.01%; N, 5.57%; found: C, 78.38%; H, 8.25%; N, 5.81%.

The product, 2,2-bis[4- [2-(4-aminophenoxy)propoxy]phenyl] propane, has the following molecular structure:

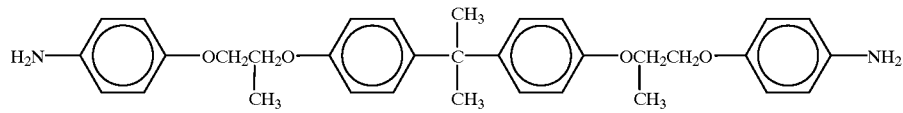

EXAMPLE 3

To a stirred solution of 0.4625 g (1.25 mmol) of 2,2-Bis [4-[2-(4-aminophenoxy)ethoxy]phenyl]propane in 10 mL of DMAc, 0.388 g (1.25 mmol) of 4,4'-oxydiphthalic anhydride (OPDA) was added gradually. The mixture was stirred at room temperature for 2–4 hours under argon atmosphere. The inherent viscosity of the poly(amic acid) in DMAc was 1.27 dL g$^{-1}$, measured at a concentration of 0.5 g dL$^{-1}$ at 30° C. The poly(amic acid) solution thus obtained was coated on a glass plate and the solvent was removed at 80° C. over night. Imidization was carried out by thermal cyclodehydration of the poly(amic acid) film, wherein the poly(amic acid) film was heated in sequence at 110, 150, 180, 210, and 260° C. for 30 minutes at each temperature. The inherent viscosity of the polyimide in concentrated H$_2$SO$_4$ (98%) was 0.65 dL g$^{-1}$, measured at a concentration of 0.5 g dL$^{-1}$ at 30° C. The IR spectrum (KBr) exhibited absorption at 1778 and 1721 cm$^{-1}$ (imide C=O), 1345 cm$^{-1}$ (C—N).

Elemental analysis data: calc.: C, 73.06%; H, 4.66%; N, 3.63%; found: C, 72.01%; H, 4.80%; N, 3.51%.

Other properties are described as follows:

Mechanical strength:

tensile strength=89 MPa elongation at break=6% initial modulus=1.25 GPa

Thermal properties:

glass transition temperature: 252° C.

10% thermal weight loss temperature: 473° C. in nitrogen and 471° C. in air char yield at 800° C. in nitrogen: 18%

The polyimide has the following molecular structure (III):

and 2 mL acetic anhydride and 1 mL pyridine were added thereto. The resulting mixture was poured to methanol, and polyimide precipitate was formed. The inherent viscosity of the polyimide in DMAc was 0.76 dL g$^{-1}$, measured at a concentration of 0.5 g dL$^{-1}$ at 30° C. The IR spectrum (KBr) exhibited absorption at 1769 and 1712 cm$^{-1}$ (imide C=O), 1345 cm$^{-1}$ (C—N).

Elemental analysis data: calc.: C, 73.30%; H, 5.27%; N, 3.49%; found: C, 72.50%; H, 5.51%; N, 3.59%.

Other properties are described as follows:

Thermal properties:

glass transition temperature: 271° C.

10% thermal weight loss temperature: 475° C. in nitrogen and 476° C. in air char yield at 800° C. in nitrogen: 20%

The polyimide has the following molecular structure (IV):

(III)

The value of m in the polymer structure can be determined from the molecular weight and molecular weight distribution obtained by size-exclusion chromatography (GPC) measurement.

The other polyimides prepared from 2,2-Bis[4-[2-(4-aminophenoxy)ethoxy]phenyl]propane with various dianhydrides were prepared in a similar way.

(IV)

| dianhydride | Tg (° C.) | 10% thermal weight loss temperature (° C.) | |
| --- | --- | --- | --- |
| | | In N$_2$ | In Air |
| PMDA | 314 | 473 | 471 |
| BPDA | 285 | 479 | 473 |
| DSDA | 279 | 466 | 455 |
| 6FDA | 269 | 468 | 466 |

EXAMPLE 4

To a stirred solution of 0.628 g (1.25 mmol) of 2,2-Bis[4-[2-(4-aminophenoxy)propoxy]phenyl]propane in 10 mL of DMAc, 0.388 g (1.25 mmol) of 4,4'-oxydiphthalic anhydride (OPDA) was added gradually. The mixture was stirred at room temperature for 2 hours under argon atmosphere, The value of m in the polymer structure can be determined from the molecular weight and molecular weight distribution obtained by size-exclusion chromatography (GPC) measurement.

The other polyimides prepared from 2,2-Bis[4-[2-(4-aminophenoxy)propoxy]phenyl]propane with various dianhydrides were prepared in a similar way.

The solubility of polyimides prepared in Examples 3 and 4 in various organic solvents were examined and the results are shown in the following table.

| Samples | Tg | Solubility[a] | | | |
|---|---|---|---|---|---|
| | | NMP | DMAc | DMF | m-Cresol |
| III (ethoxy group containing) | 252 | – | – | – | – |
| IV (propoxy group containing) | 271 | + | + | + | + |

[a] –: insoluble; +: soluble; NMP: N-methyl-2-pyrrolidone; DMAc: N,N-dimethylacetamide; DMF: dimethylformamide.

What we claim is:

1. A diamine having a chemical formula as follows:

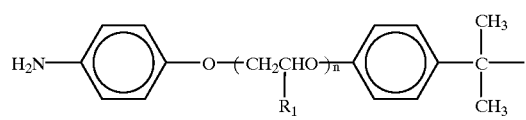

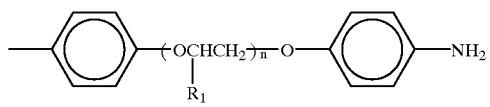

wherein $R_1$ is methyl ($CH_3$); and n is an integer ranging from 1 to 4.

2. The diamine according to claim 1, wherein n is 1.

* * * * *